United States Patent [19]

Cherniak

[11] Patent Number: 5,263,496
[45] Date of Patent: Nov. 23, 1993

[54] PATIENT SUPPORT PAD FOR EASING PAIN

[76] Inventor: Trexie I. Cherniak, 1810 SW. 81st Ave., Apt. 2116, North Lauderdale, Fla. 33068

[21] Appl. No.: 952,470

[22] Filed: Sep. 28, 1992

Related U.S. Application Data

[63] Continuation of Ser. No. 772,072, Oct. 7, 1991, abandoned.

[51] Int. Cl.⁵ .................. A61G 15/00; A61F 5/37; A47C 20/00
[52] U.S. Cl. ..................... 128/845; 128/876; 5/630
[58] Field of Search ............ 128/876, 96.1, 100.1, 128/845; 2/84, 94; 602/16, 19; 5/489–492, 494, 630, 631, 632

[56] References Cited

U.S. PATENT DOCUMENTS

| | | | |
|---|---|---|---|
| 1,380,480 | 6/1921 | Jennings | 5/490 |
| 2,250,267 | 7/1941 | Lins | 5/431 |
| 3,945,041 | 3/1976 | Rhee | 128/78 |
| 4,294,239 | 10/1981 | Oram | 128/96.1 |
| 4,467,477 | 8/1984 | DeGennaro | 2/94 |
| 4,506,396 | 3/1985 | Ritchie | 5/431 |
| 4,683,601 | 8/1987 | Lagin | 5/431 |
| 4,736,477 | 4/1988 | Moor | 128/88 |
| 4,934,005 | 6/1990 | Martin | 5/431 |
| 4,951,998 | 8/1990 | McClain | 5/437 |
| 4,959,880 | 10/1990 | Tesch | 5/437 |

Primary Examiner—Michael A. Brown
Attorney, Agent, or Firm—Malin, Haley, DiMaggio & Crosby

[57] ABSTRACT

An abdominal support for reducing pain of a surgery patient while increasing mobility and support of a conformable pillow to the abdominal section that comprises a fabric waist band sized to fit comfortably around the upper and middle torso of the wearer and a conformable and deformable pillow preferably stuffed with feathers or man made fibers which provide a comfortable yet support pillow for the wearer which is attached to the fabric waist band. The device includes fabric fasteners for proper pressure adjustment in strategic areas.

4 Claims, 1 Drawing Sheet

PATIENT SUPPORT PAD FOR EASING PAIN

This is a continuation of copending application(s) Ser. No. 07/772,072 filed on Oct. 7, 1991 now abandoned.

BACKGROUND OF THE INVENTION

1. Field of the Invention

This invention relates to a support pad for use by a patient after a surgical operation especially in the chest or abdominal area for supporting the chest area or the abdominal area with a pad in a hands free mode.

2. Description of the Prior Art

After a surgical operation, the patient can be in severe pain based on any movements in or out of bed, sitting or walking. One form of relief that has been found is for the patient to use a conventional pillow, using one arm or hand as a pillow support while walking, sitting or movement of any type after surgery that presses the pillow against the abdominal or stomach area for support to relieve the pain. Often when walking or getting in and out of bed or in any type movement, especially with an intravenous (IV) pole or the like, it is impossible to support oneself or move oneself with one arm while trying to support the pillow with the other arm for relieving pain.

Support devices are known in the prior art. U.S. Pat. No. 4,467,477 issued Aug. 28, 1984 to DeGennaro for Foldable Wearing Apparel shows a device to secure an article of wearing apparel to a person. U.S. Pat. No. 4,736,477 shows a knee pillow to prevent shaping which allows a pillow to be attached in the knee area of the user. U.S. Pat. No. 4,294,239 shows an abdominal support utilizing a pre-formed pad of a predetermined shape that has been molded or otherwise formed of a sturdy material.

The prior art utilized pads which did not provide sufficient resilience that will allow one to adjust a resilient pillow that includes feathers and fibers or a very resilient material that can be shaped to the particular configuration of the user so that the user can eliminate pain while still supporting (hands free) particular areas of the body with a pillow.

SUMMARY OF THE INVENTION

An abdominal support for a deformable resilient cushion or pillow having a first section with a pillow containing feathers, fibers or other very resilient and conformable material sized to fit from the upper torso area to below the mid-torso area of a person. The pillow is attached to an adjustable broad fabric band that can encompass the torso and particularly the waist area of a person with a pair of fabric fasteners (such as VELCRO) attached at the first end of the fabric band and to an upper outside area of the pillow which allows it to be adjusted across the waist in size while firmly holding the pillow in the forward waist area of the user. The fabric waist band may be made of cotton or any other suitable natural or synthetic material and should be sized to be approximately the size of the pillow to offer additional support around the maximum waist area of the user with minimum discomfort. The entire unit with the pillow and the waist band made of fabric will fit snugly around the body of the user. As an alternative to the fabric fasteners, tie straps could be employed if desired.

It is very important that the pillow have a fabric encasement or enclosure that does not irritate or feel rough to the skin and that the interior contents such as feathers or fibers prevent a soft conformable pillow that will adjust to the shape of the wearer. This is especially important to provide the proper support, reduce specific pressure on the wearer and reduce pain to the wearer.

It is an object of this invention to provide an improved abdominal support which allows the wearer to develop a configuration or conformity of the pillow to the body of the wearer.

It is another object of this invention to provide an easily usable abdominal support pillow and waist band that allows a surgery patient to increase the person's mobility while easing pain from the surgery through the support of the pillow and waist band.

And yet another object of this invention is to allow a surgery patient to have a support pillow with them at all times which does not require the constant use of one hand and arm for support purposes.

In accordance with these and other objects which will become apparent hereinafter, the instant invention will now be described with particular reference to the accompanying drawings.

BRIEF DESCRIPTION OF THE PREFERRED EMBODIMENT

Figure 1:
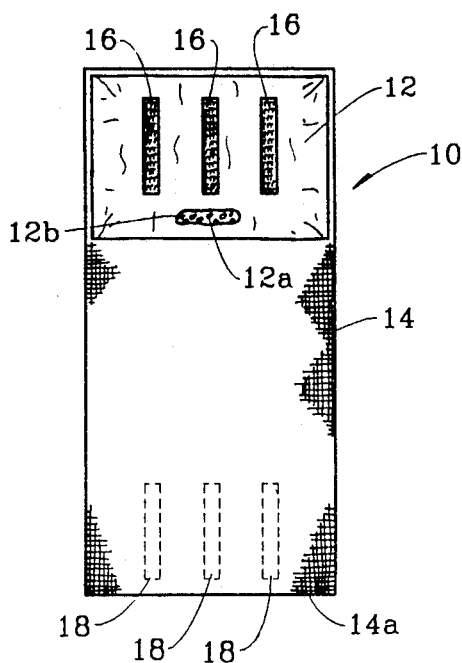
FIG. 1 shows a front plan view of the present invention.

Referring now to the drawings and specifically FIG. 1, the present invention is shown generally at 10 comprised of a pillow 12 sized to fit between the arm pits and lower torso of a person being approximately the standard size of a conventional bed pillow and containing a fabric casing made of cotton 12b that contains a plurality of feathers 12a to form a soft conformable pillow which although can be used for support, will completely conform to the waist configuration of the wearer. The pillow 12 is attached to a fabric sheet 14 which is sized in width to be equal to the top to bottom length of the pillow and which is attached to the pillow by sewing or other conventional connection so that at one end of the fabric strip 14, pillow 12 is attached firmly thereto. In addition, the fabric strip includes a plurality of hook-pile fasteners 18 at one end 14a which may be in a strip format which themselves are used to attach to a plurality of corresponding fabric fasteners 16 mounted on the pillow 12.

Figure 2:
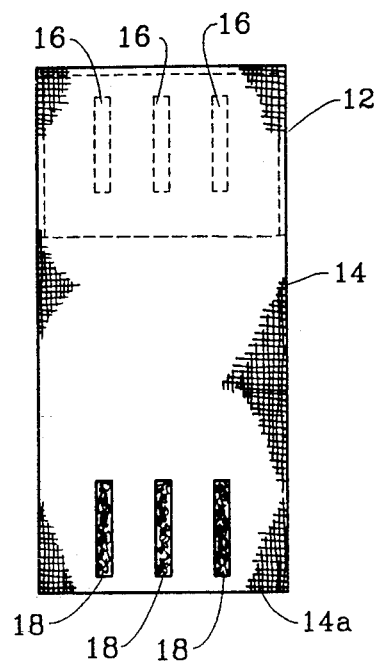
FIG. 2 shows a back plan view of the invention.

FIG. 2 shows the back side of the fabric band 14 and the relationship of the fabric fasteners 18 which are mounted on the opposite side.

Figure 3:
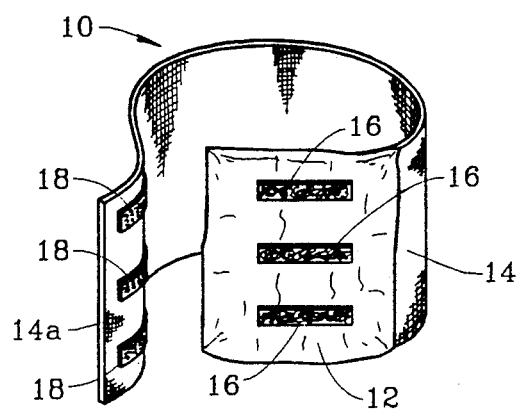
FIG. 3 shows a perspective view of the invention with the encircling waist band in the open position.

FIG. 3 shows a perspective view with the pillow 12 and fabric fasteners 16 which are permanently attached to pillow 12 and their special relationship with the hook-pile fabric fasteners 18 mounted on the free end 14a of waist band 14. The long narrow fabric fastener strips 16 and 18 ensure that the waist band 14 can be properly adjusted to insure that it stays in position around the waist of a wearer.

Figure 4:
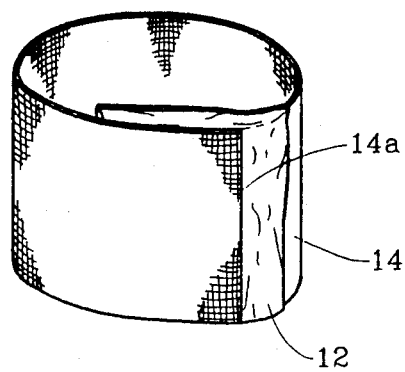
FIG. 4 shows a perspective view of the invention with the waist band in a closed position.

FIG. 4 shows the free end 14a firmly attached by fabric fasteners to pillow 12 in a condition where the wearer would have it tightly around the waist.

Figure 5:
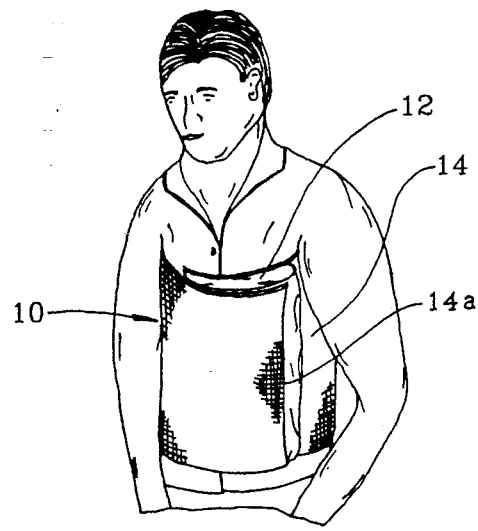
FIG. 5 shows a front view of the invention as it would be employed around the waist of a wearer.

Looking at FIG. 5, the invention is shown as a large waist band 14 disposed around the wearer in a position to provide contour but support on the front abdominal area of the wearer. Note that the invention can readily be conformed provided that the pillow is sufficiently conformable through the use of feathers or proper fibers to achieve the exact comfort level required by the wearer without being a rigid hard foam cushion which could be uncomfortable or cause harm to the patient.

Once the invention 10 is in place in the wearer as shown in FIG. 5, the wearer can freely move about and not require hand or arm support of the cushion while it is in place firmly by waist band 14. Notice also that the full length waist band 14 provides for support across the entire torso so that it is not apt to slide down or fall from the wearer. Thus, in one embodiment as shown in FIG. 5, the size of the pillow and the waist band are similar in width and height.

To use the present invention, the wearer need only have assistance with the waist strap 14 surrounding the wearer's body and the pillow conformably positioned in the front area of the wearer so it is comfortable with the fabric fasteners then being engaged on the waist band to achieve the right fasteners and tension to hold the pillow comfortably in place for the wearer.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. An abdominal support device for a surgery patient comprising:
   an adjustable broad fabric waist band, sized to encompass the torso of the patient:
   a pillow including its own fabric enclosure, the fabric enclosure constructed of a material which will not irritate or feel rough to the skin of the surgery patient, said pillow including a stuffing material such as feathers to provide a conformable pillow whose outer surface can be configured to adjust to changing surface of a wearer, said pillow being attached to the side of said fabric waist band, said pillow being sized to reach only from the upper or lower arm pit area to the lower torso of the wearer in length and from side to side of a wearer in width, said waist band being sized from the arm pit of the wearer to at least the hip area whereby the entire pillow can be supported with the waist band comfortably around the wearer, and means connected to one end of the waist band and to one side of said pillow fabric enclosure for adjusting the waist band length to fit the surgery patient comfortably, to hold the pillow in place in the front abdominal area of the patient, hands free.

2. An abdominal support device for a surgery patient as in claim 1, wherein:
   said means for adjusting the waistband length to fit the surgery patient including at least two elongated strips attached adjacent the free end of the waistband on one side, each of said strips being a hook fabric fastener;
   a pair of pile fabric fastener strips substantially elongated and aligned with respect to a longitudinal axis of said waistband attached to one side of said pillow, facing outwardly so that the free end of the waistband can be positioned longitudinally with respect to said fabric hook fastener strips relative to the elongated fabric strips on said pillow for comfortable, hands-free support of said pillow in the front of said patient about said patients waist.

3. An abdominal support for a surgery patient as in claim 2, wherein:
   said fabric waistband is made of a cotton fabric and is sized in width to attach to a substantial portion of said pillow.

4. The abdominal support device of claim 1 wherein said fabric enclosure constructed from a cotton material.

* * * * *